(12) United States Patent
Ruan et al.

(10) Patent No.: US 11,702,690 B2
(45) Date of Patent: Jul. 18, 2023

(54) SEQUENCING LIBRARY, AND PREPARATION AND USE THEREOF

(71) Applicant: Agricultural Genomics Institute at Shenzhen China Academy of Agricultural Sciences, Guangdong (CN)

(72) Inventors: Jue Ruan, Guangdong (CN); Kaile Wang, Guangdang (CN)

(73) Assignee: Agricultural Genomics Institute at Shenzhen China Academy of Agricultural Sciences, Guangdong (CN)

(*) Notice: Subject to any disclaimer, the term of this patent is extended or adjusted under 35 U.S.C. 154(b) by 1017 days.

(21) Appl. No.: 15/903,911

(22) Filed: Feb. 23, 2018

(65) Prior Publication Data

US 2019/0078157 A1 Mar. 14, 2019

Related U.S. Application Data

(63) Continuation of application No. PCT/CN2015/095380, filed on Nov. 24, 2015.

(30) Foreign Application Priority Data

Sep. 30, 2015 (CN) .......................... 201510638417.5

(51) Int. Cl.
*C12Q 1/6869* (2018.01)
*C40B 40/06* (2006.01)
(Continued)

(52) U.S. Cl.
CPC .......... *C12Q 1/6869* (2013.01); *C12N 15/10* (2013.01); *C12N 15/1065* (2013.01);
(Continued)

(58) Field of Classification Search
CPC .......................... C12N 15/10; C12N 15/1065; C12N 15/1068; C12N 15/1086; C12N 15/1089;
(Continued)

(56) References Cited

U.S. PATENT DOCUMENTS 5,176,996 A * 1/1993 Hogan ............... C12N 15/1138
536/25.1
8,080,393 B2 12/2011 Koch et al.
(Continued)

FOREIGN PATENT DOCUMENTS

CN 1793376 A 6/2006
CN 101213310 A 7/2008
(Continued)

OTHER PUBLICATIONS

Lou et al. (Proc. Natl. Acad. Sci., 2013, 112(49): 19872-19877 (Year: 2012).*
(Continued)

*Primary Examiner* — Jeremy C Flinders
(74) *Attorney, Agent, or Firm* — Standley Law Group LLP; Adam J. Smith (57) ABSTRACT

The present invention discloses a sequencing library comprising a nucleotide sequence. The sequence comprises a linker sequence and two target sequences. Two ends of the linker sequence are respectively linked to the target sequences and the two target sequences are direct repeat sequences. The present invention further discloses preparation and use of the sequencing library. The present invention overcomes the high error rate problem of current DNA sequencing technologies, especially in a way of very low coverage bias, and can be used to detect low frequency mutations in different kinds of samples.

8 Claims, 2 Drawing Sheets

Specification includes a Sequence Listing.

(51) Int. Cl.
    *C40B 50/06*     (2006.01)
    *C12N 15/10*     (2006.01)
    *C12Q 1/68*     (2018.01)
    *C12Q 1/6806*     (2018.01)
    *C12Q 1/686*     (2018.01)

(52) U.S. Cl.
    CPC ..... *C12N 15/1068* (2013.01); *C12N 15/1086* (2013.01); *C12N 15/1089* (2013.01); *C12N 15/1093* (2013.01); *C12Q 1/68* (2013.01); *C12Q 1/6806* (2013.01); *C40B 40/06* (2013.01); *C40B 50/06* (2013.01); *C12N 2310/3517* (2013.01); *C12N 2320/10* (2013.01); *C12Q 1/686* (2013.01); *C12Q 2521/501* (2013.01); *C12Q 2521/514* (2013.01); *C12Q 2600/16* (2013.01); *C12Q 2600/166* (2013.01)

(58) Field of Classification Search
    CPC ........ C12N 2310/3517; C12N 2320/10; C12Q 1/68; C12Q 1/6806; C12Q 1/686; C12Q 1/6869; C12Q 2521/501; C12Q 2521/514; C12Q 2600/16; C12Q 2600/166; C40B 40/06; C40B 50/06
See application file for complete search history.

(56) References Cited

U.S. PATENT DOCUMENTS

| | | |
|---|---|---|
| 8,530,197 B2 | 9/2013 | Li et al. |
| 9,657,291 B2 | 5/2017 | Li et al. |
| 10,190,164 B2 | 1/2019 | Li et al. |
| 2013/0252851 A1 | 9/2013 | Li et al. |
| 2019/0226022 A1 | 7/2019 | Li et al. |

FOREIGN PATENT DOCUMENTS

| | | | |
|---|---|---|---|
| CN | 102016068 | A | 4/2011 |
| CN | 102286456 | A | 12/2011 |
| CN | 102534811 | A | 7/2012 |
| CN | 102628079 | A | 8/2012 |
| CN | 104532360 | A | 4/2015 |
| CN | 104561362 | A | 4/2015 |
| CN | 104695027 | A | 6/2015 |
| CN | 104726549 | A | 6/2015 |
| CN | 105420348 | A | 3/2016 |
| CN | 107002291 | A | 8/2017 |
| CN | 107002292 | A | 8/2017 |
| CN | 108138364 | A | 6/2018 |
| WO | WO-2010048337 A2 * | | 4/2010 ........... C12Q 1/6855 |

OTHER PUBLICATIONS

TruSeq (TruSeq(R) DNA Sample Preparation Guide, Illumina, 2012) (Year: 2012).*
Schmitt et al. (Proc. Natl. Acad. Sci., 2012, 109(36):14508-14513) (Year: 2012).*
Sun et al. (Comput. Struct. Biotechnol. J., 2014, 11 (18):66-72) (Year: 2014).*
Lobanenkov et al. (Oncogene, 1990, 5:1743-1753) (Year: 1990).*
Cox et al. (Proc. Natl. Acad. Sci. USA, 1997, 94:5237-5242) (Year: 1997).*
Kinde, I. et al., Detection and Quantification of Rare Mutations With Massively Parallel Sequencing, PNAS, Jun. 7, 2011, pp. 9530-9535, vol. 108, No. 23.
First Notification of Office Action, National Intellectual Property Administration, PRC, dated Oct. 8, 2018, Chinese Patent Application No. 201510638417.5.

* cited by examiner

SEQUENCING LIBRARY, AND PREPARATION AND USE THEREOF

CROSS-REFERENCE TO RELATED APPLICATIONS

This application is a continuation application of, and claims priority to, International Application No. PCT/CN2015/095380 filed on Nov. 24, 2015, which claims the priority of Chinese Patent Application No. 201510638417.5 entitled "Sequencing library, and preparation and use thereof" filed on Sep. 30, 2015 with the State Intellectual Property Office of the P. R. China, the contents of which are incorporated herein by reference in its entirety their entireties.

BACKGROUND

Technical Field

The present invention relates to a sequencing library, and preparation and use thereof.

Related Art

The development of the next generation sequencing technology has promoted the revolutionary advancement in biology and biomedical research. However, due to the characteristics of high-throughput sequencing, there is about 1% base error in the measured sequence. Although the 1% error rate is acceptable in some applications, this 1% error makes a lot of real information hidden in many cases and becomes a barrier in many studies, for example, in the process of microbial mutagenesis, how to monitor a distribution mode of mutation frequency caused by a mutagenic agent at various mutagenic concentrations, to effectively optimize the mutagenesis system and improve the mutagenesis efficiency; how to screen a target bacterial strain with a target mutation in a large mutagenic population; and in detecting whether there is a potential oncogenic mutation site in a tissue or organ in a normal individual; in detecting the heterogeneity of DNA composition and the hidden small clonal populations in the cancer cell population, in using the DNA mutations in each cell as a marker to trace the origin and the pattern of division of the cell, in accurately genotyping a highly heterozygous cancer population, in calculating the rate of mutation upon division of cancer cells or somatic cells, in searching for pathogenic mutations in some small populations such as cancer stem cells in the biomedical therapies, in screening or detecting pathogenic and carcinogenic mutations in free DNA in peripheral blood, and in early prediction of the diseases. Therefore, how to accurately determine the DNA sequence by using the existing next generation sequencing technology has become a very critical issue.

Till now, there are some methods that endeavor to biologically or chemically improve the errors originated from the next generation sequencing, such as the method of library construction without amplification, by which the errors caused by polymerase chain reaction (PRC) amplification during the library preparation are effectively avoided. The sample DNA and reference DNA are tagged appropriately to effectively filter out chain-specific errors. In some methods, the error rate of the next generation sequencing is reduced by data analysis. In addition, in some other methods, the errors due to PCR amplification are corrected with breakpoint information generated when DNA is randomly fragmented or by tagging the DNA template prior to the PCR amplification. Which DNA molecules are derived from the same molecule can be determined by tagging, thereby achieving the purpose of correcting the errors.

To some extent, these methods improve the accuracy of next generation sequencing. However, these methods suffer from respective defects, as shown in the article of Kinde I, et al. (Kinde I, Wu J, Papadopoulos N, Kinzler K W, Vogelstein B (2011) Detection and quantification of rare mutations with massively parallel sequencing. Proc Natl Acad Sci USA 108:9530-9535). In the method of tagging, a tag is added to the terminus of a specific primer, and then to a DNA molecule by PCR. When errors occur during the PCR reaction for adding the tag, such errors are difficult to remove in later experiments, which limits the detection for sites of extremely low frequency. A major limitation in exogenously tagging the DNA is that this method can only target a small genome or a few genes of interest and cannot achieve a complete detection of the entire genome. Because in the tagging method, the same and complementary tags need to be detected to achieve the purpose of mutual calibration of DNA positive and negative strands, an extremely high depth of sequencing is required, which is very difficult for a large genome.

In this regard, Ruan Jue, Wang Kaile, et al. develop a DNA library construction method (Chinese Patent Application No. 201310651462.5), in which a single strand of a DNA molecule is circularized, and then subjected to rolling circle amplification, the products copied from the same molecule are connected in tandem, and the errors generated in the library construction and sequencing are corrected and removed by using the separate sequencing information of a preceding and a following copy, thereby effectively reducing the error rate of sequencing and increasing the data utilization. However, the bias of rolling circle amplification greatly limits the use thereof. In the following experiments, Wang Kaile, Ruan Jue, et al. make further improvements on the bias of rolling circle amplification (Chinese Patent Application No. 201410448968.0), and the bias of rolling circle amplification is reduced to a certain extent. However, the large bias of rolling circle amplification is still not well resolved. Rolling circle amplification has a great sequence bias, such that the amplification multiple of some circular DNAs is very large while the amplification multiples of most circles is very low. Therefore, it is difficult to achieve a comprehensive, effective and accurate detection of the entire genome in the subsequent sequencing.

In summary, it is necessary to develop a sequencing library that can rapidly, efficiently and accurately determine DNA sequences.

SUMMARY

The present invention provides a sequencing library, and preparation and use thereof, to solve the problem that the accuracy of DNA sequencing in the prior art cannot meet the actual need.

Unless otherwise particularly defined herein, the related terms used in the present invention have the following definitions.

As used herein, the term "target sequence" refers to an insert fragment of a sequencing library provided in the present invention as a sequence of a sequencing target.

As used herein, the term "adaptor sequence" refers to a sequence designed in the present invention to connect to one or both ends of a target sequence for circularization of the target sequence. The adaptor sequence in the present invention may be designed as a single-stranded adaptor or as a double-stranded adaptor, and when it is double-stranded, the double-stranded adaptor is formed by annealing two single-stranded nucleotide sequences that are at least partially complementary. In the present invention, the adaptor sequence can be designed by those skilled in the art according to the selected enzyme and reaction conditions and based on the conventional technical means in the art. In the prepared double-stranded circular nucleotide sequence, the melting temperature (Tm) of two strands of the region between the gaps should be higher than the reaction temperature of the used strand displacement enzyme. In one embodiment of the present invention, the adaptor sequence is, for example, as shown in SEQ ID NO: 1 and/or SEQ ID NO: 2. In embodiments of the present invention, when designed as a double-stranded adaptor sequence, two adaptor sequences are annealed to yield a double-stranded adaptor sequence, and the ligation product of the target sequence that needs to be circularized and the adaptor sequence need to be phosphorylated at the 5' end.

As used herein, the term "linker" refers to a sequence that links, in a chained double-stranded nucleotide sequence obtained from a double-stranded circular nucleotide sequence prepared in the present invention, the target sequences at two ends. A reverse complementary sequence exists in at least part of the region of the linker.

As used herein, the term "sequencing length of DNA sequencing machine" refers to a sequencing length of the DNA sequencing machine that is equal to the sum of the paired-end read lengths for paired-end sequencing; and a sequencing length of the DNA sequencing machine that is equal to the single-end read length for single-end sequencing.

As used herein, the term "nicking endonuclease" refers to that in contrast to a fact that when a restriction endonuclease binds to a DNA recognition sequence, both strands of DNA are hydrolyzed at the same time, because each endonuclease has two functional domains for hydrolysis, which act on two strands of DNA and catalyze a hydrolysis reaction respectively, the nicking endonucleases hydrolyzes only one strand of double-stranded DNA and nicks the DNA strand, and the nicking produces 3'-hydroxyl and 5'-phosphate.

As used herein, the term "nicking site" refers to a site which is cleavable in the nucleotide sequence for a single-stranded nucleotide sequence; and a site which is cleavable in one strand while the corresponding site is non-cleavable in the other strand for a double-stranded nucleotide sequence.

As used herein, the term "gap" refers to a non-contiguous region in a double-stranded nucleotide sequence, and the length of the gap may be one or more bases.

As used herein, the term "sequencing library" refers to a collection of DNA fragments for sequencing containing the target sequences and other sequences (for example, sequencing adaptors).

One aspect of the present invention relates to a single-stranded circular nucleotide sequence having at least one nicking site.

In a specific embodiment, the single-stranded circular nucleotide sequence has one nicking site.

In a specific embodiment, the nicking site may be a dUTP base, 8-oxo-dGTP or a nicking endonuclease recognition site.

One aspect of the present invention relates to a double-stranded circular nucleotide sequence having at least one nicking site or a gap in each strand.

In a specific embodiment, the double-stranded circular nucleotide sequence has a gap in one strand (strand 1), and the other strand (strand 2) has at least one nicking site. Specifically, the position of the nicking site in strand 2 is at the upstream of the gap in strand 1 (for example, in FIG. 1, nicking site "2" is at the upstream of gap "1") to make sure the amplified DNA in strand displacement amplification step is target DNA, not only linker sequence.

In a specific embodiment, both strands of the double-stranded circular nucleotide sequence have at least one nicking site.

In a specific embodiment, both strands of the double-stranded circular nucleotide sequence have a gap.

In specific embodiments, the closest distance between the gap/nicking site on one strand of the double-stranded circular nucleotide sequence and the gap/nicking site on the other strand is preferably greater than 6 bases.

In specific embodiments, the nicking site may be a dUTP base, 8-oxo-dGTP or a nicking endonuclease recognition site.

One aspect of the present invention relates to a nucleotide sequence comprising a linker and two target sequences, in which two ends of the linker are respectively linked to the target sequences and the two target sequences are direct repeat sequences.

In a specific embodiment, the linker has a reverse complementary region.

In specific embodiments, one end of at least one of the target sequences opposing the end linked with the adaptor sequence may be further linked with an additional sequence, where at least part of the region of the additional sequence is the same as part of the region of the linker.

In specific embodiments, the length of the target sequence is less than the sequencing length of a DNA sequencing machine.

In specific embodiments, the sum of the lengths of the additional sequence and the target sequences is less than the sequencing length of a DNA sequencing machine.

One aspect of the present invention relates to a nucleotide sequence consisting of a linker and target sequences linked to two ends of the linker, where the two target sequences are direct repeat sequences. The length of the target sequence is less than the sequencing length of a DNA sequencing machine.

One aspect of the present invention relates to a nucleotide sequence consisting of a linker and two target sequences, where two ends of the linker are respectively linked to the target sequences and part of the regions of the two target sequences are direct repeat regions.

One aspect of the present invention relates to a sequencing library comprising any one of the nucleotide sequences.

One aspect of the present invention relates to an adaptor sequence having at least one nicking site in the case where other nucleotides are connected to two ends.

In specific embodiments, the adaptor sequence is 6-100 bp.

In specific embodiments, the adaptor sequence may be a double-stranded nucleotide sequence.

One aspect of the present invention relates to use of the adaptor sequence in the preparation of the single-stranded circular nucleotide sequence, the double-stranded circular nucleotide sequence, the nucleotide sequence, the nucleotide sequence or the sequencing library.

One aspect of the present invention relates to application of the single-stranded circular nucleotide sequence in the preparation of the double-stranded circular nucleotide sequence, the nucleotide sequence, the nucleotide sequence or the sequencing library.

One aspect of the present invention relates to application of the double-stranded circular nucleotide sequence in the preparation of the nucleotide sequence, the nucleotide sequence or the sequencing library.

One aspect of the present invention relates to application of the nucleotide sequence in the preparation of the nucleotide sequence or the sequencing library.

One aspect of the present invention relates to application of the nucleotide sequence in the preparation of the sequencing library.

One aspect of the present invention relates to a method for preparing the single-stranded circular nucleotide sequence, comprising the following Steps:

Ligate a target sequence with an adaptor sequence containing a nicking base, a nicking restriction site or a gap, to obtain a double-stranded or single-stranded DNA; when the obtained DNA is a double-stranded sequence, denaturing to form a single-stranded sequence, followed by single-stranded circularization; and when the obtained DNA is a single-stranded sequence, performing single-stranded circularization directly.

One aspect of the present invention relates to a method for preparing the double-stranded circular nucleotide sequence, comprising the following Steps:

synthesizing a complementary strand of the single-stranded circular nucleotide sequence by using a primer which is not phosphorylated at the 5' end, to form a double-stranded circular structure with a nicking site or a gap; or performing double-stranded circularization directly on the double-stranded sequence, obtained by ligate the target sequence with the adaptor sequence containing a nicking site, a nicking endonuclease recognition site or a gap.

One aspect of the present invention relates to a method for preparing the nucleotide sequence, comprising the following Steps:

nicking the double-stranded circular nucleotide sequence to obtain a double-stranded circular nucleotide sequence having nicks or gaps in both strands; and subjecting the double-stranded circular nucleotide sequence having nicks or gaps in both strands to strand displacement amplifications.

One aspect of the present invention relates to a method for preparing the sequencing library, comprising the Steps of: subjecting the nucleotide sequence to end-repair A-tailing, and ligate with the sequencing adaptor, followed by PCR.

One aspect of the present invention relates to use of the sequencing library in gene sequencing. The gene sequencing includes, but is not limited to, genomic DNA sequencing, target fragment capture sequencing (e.g., exon capture sequencing), single-stranded DNA fragment sequencing, fossil DNA sequencing or sequencing of free DNA in body fluids (e.g., blood, urine, and saliva).

One aspect of the present invention relates to a sequencing method comprising the Step of using the sequencing library.

One aspect of the present invention relates to a sequencing kit comprising an end repair A-tailing reagent, a DNA ligase, an adaptor sequence, a single-stranded circularization reagent, a nickase, and a strand displacement reagent.

Figure 1:
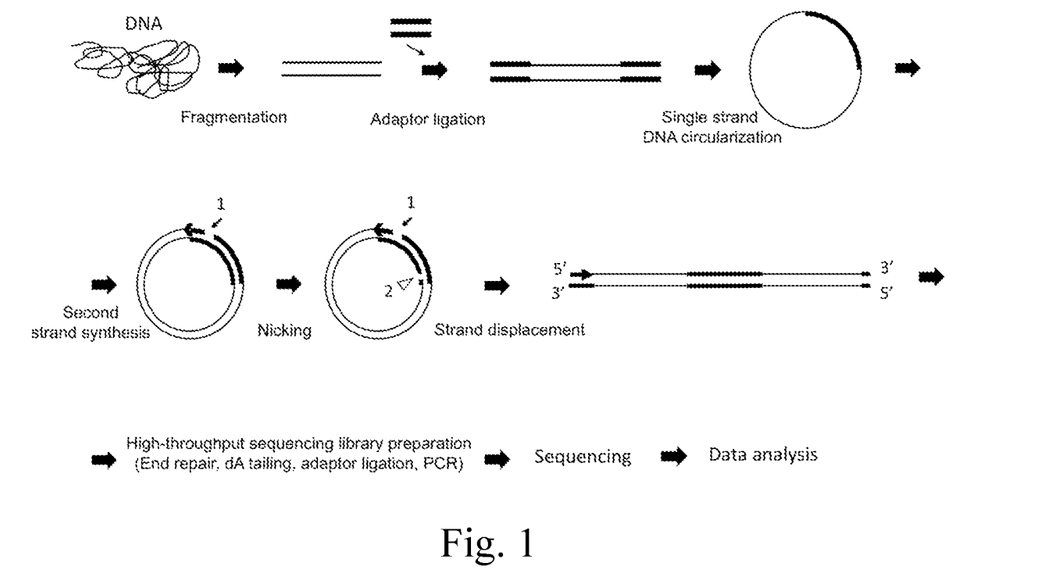
Figure 2:
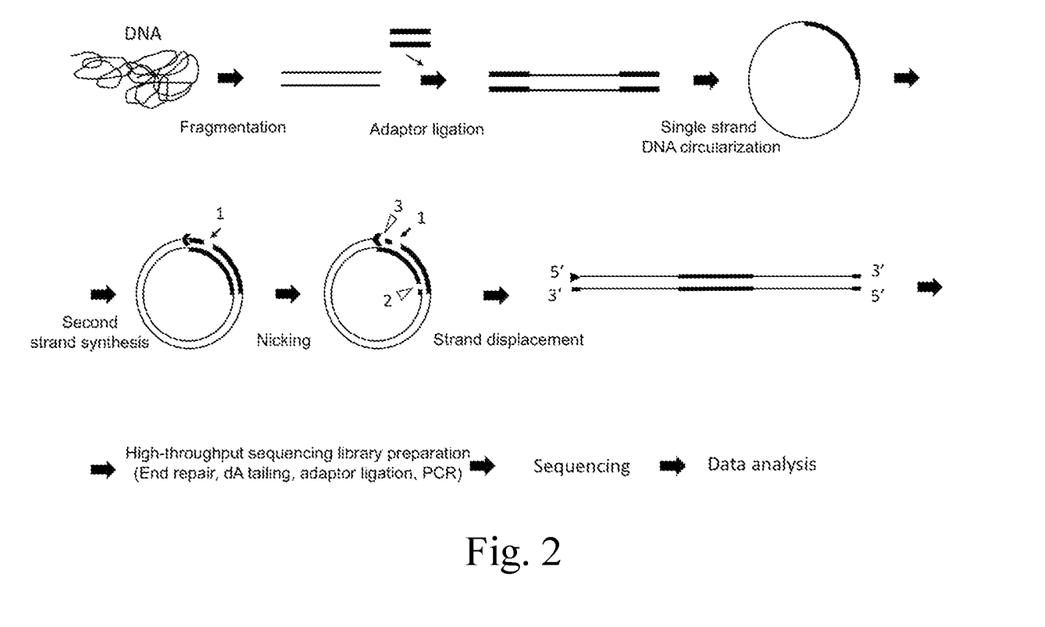
Figure 3:
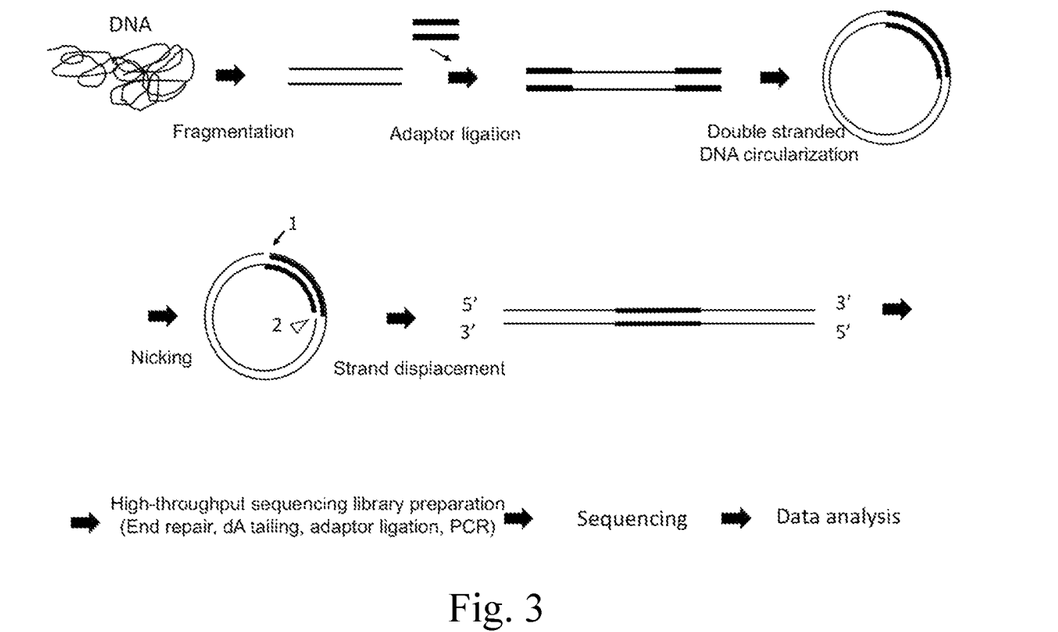
FIG. 3 is a flow chart of a process for constructing a sequencing library according to the present invention (by using a primer with a nicking base). A DNA macromolecule is fragmented and ligated to an adaptor with a nicking base (such as dUTP, 8-oxo-dGTP, and nicking endonuclease recognition site, etc.), followed by double-stranded circularization. For the circularized DNA molecule, a gap is generated by nicking (where according to the nicking base in the adaptor, an appropriate nicking mode is selected), and the sequence consisting of the linker and two copies of the target sequence is subjected to strand displacement synthesis. A standard high-throughput sequencing library is constructed by using the double-stranded DNA after the strand displacement, and sequenced, and the data is analyzed.

An embodiment of the present invention provides a method for preparing the sequencing library, comprising the Steps of:

(1) ligate a target sequence with an adaptor sequence (containing a nicking site, a nicking endonuclease recognition site or a gap) to obtain a double-stranded or single-stranded DNA;

(2) circularizing the DNA obtained in Step (1), where when the DNA obtained in Step (1) is a double-stranded sequence, double-stranded circularization is performed directly or single-stranded circularization is performed after the double-stranded sequence is denaturized to form a single-stranded sequence; and when the DNA obtained in Step (1) is a single-stranded sequence, single-stranded circularization is performed directly;

(3) when single-stranded circularization is performed, synthesizing a complementary strand of the circularized DNA obtained in Step (2) by using a primer which is not phosphorylated at the 5' end, to form a double-stranded circular DNA with a gap (gap 1), as shown in FIGS. 1 and 2; and when double-stranded circularization is performed, the product after the double-stranded circularization having a double-stranded circular DNA, as shown in FIG. 3;

(4) nicking the double-stranded circular structure obtained in Step (3), where when the double-stranded circular DNA is obtained through the complementary strand synthesis after single-stranded circularization, a nick or a gap is formed on the DNA strand with a nicking site (gap 2); the shortest distance between the nicked gap (gap 2) and the complementary strand gap (gap 1) is preferably 6 bases or more; the nicked gap is located in the 5' direction of the complementary strand gap, as shown in FIG. 1; further, the primer for complementary strand synthesis also contains a site or sites to be cleaved, and after nicking, a nick or a gap is formed (gap 3) on the complementary strand; the nicked nick or gap on the complementary strand is preferably located in the 3' direction of the complementary strand gap, as shown in FIG. 2; and when the double-stranded circular structure is obtained by double-stranded circularization, a nick or a gap is respectively formed on two strands, for example, gap 1 and gap 2 as shown in FIG. 3;

(5) subjecting the circular DNA having nicks or gaps in two strands obtained in Step (4) to strand displacement amplification to form a nucleotide sequence in the form of 5' adaptor sequence (this adaptor sequence may not exist)-target sequence-linker-target sequence-3' adaptor sequence (this adaptor sequence may not exist), where the linker is formed by connecting the adaptor sequence linked in the preceding step; and (6) constructing a next generation or third-generation sequencing library by using the nucleotide sequence obtained in Step (5), for example, by subjecting the nucleotide sequence obtained in Step (5) to end-repair A-tailing, and ligate with a sequencing adaptor, followed by PCR, to obtain a DNA sequencing library.

In the present invention, the adaptor sequence ligated after DNA fragmentation Step (1) may be connected to the 5' end, the 3' end or both ends of the target sequence by means of single-stranded or double-stranded ligation. In the case where the adaptor sequence is ligated to both ends of the target sequence, the linker of the single-stranded circular nucleotide sequence or the double-stranded circular nucleotide sequence is formed by connecting the adaptor sequences at both ends, and the linker has a reverse complementary region. In the case where the adaptor sequence is linked to a single end of the target sequence, the linker of the single-stranded circular nucleotide sequence or the double-stranded circular nucleotide sequence is the adaptor sequence. In the case where the adaptor sequence is connected to the target sequence by single-stranded connection, a single-stranded circular nucleotide sequence is formed by direct single-stranded circularization. In the case where the adaptor sequence is ligated to the target sequence by double-stranded ligation, the double-strand sequence is denatured into a single-stranded sequence, which is then circularized to obtain a single-stranded circular nucleotide sequence. The process can be implemented by those skilled in the art according to conventional technical means in the art.

In the present invention, in the double-stranded circular nucleotide sequence, the adaptor sequence connected contains a nicking site or an existing nick or gap.

The circularization method in the present invention may be single-stranded circularization or double-stranded circularization.

When single-stranded circularization is used, the synthesis of a complementary strand is required. When the complementary strand is synthesized, the primer used is a primer which is not phosphorylated at the 5' end. The primer may or may not contain a base capable of forming a nicking site (such as dUTP, and 8-oxo-dGTP, etc.) or a nicking endonuclease recognition site (e.g. 5'-GC ▲ TGAGG-3' of nicking endonuclease Nb.BbvCI), and the primer may match with part of the region of the adaptor sequence, or match with a known sequence in the target sequence. When double-stranded circularization is used, since the circularized DNA is double-stranded, complementary strand synthesis is not required.

In the present invention, there are many approaches to generate nick or gap. For example, in primers used for complementary strand synthesis and adaptor sequence, one or more bases such as dUTP and 8-oxo-dGTP are designed to form nicks or gaps by nicking using dUTP and 8-oxo-dGTP nicking enzymes (e.g., UDG, USER enzyme, etc.) after the complementary strand is synthesized; in primers used in the complementary strand synthesis and the adaptor sequence, nicking endonuclease recognition sites are designed, so as to generate nicks or gaps by nicking using DNA nicking endonuclease and so on.

In the present invention, strand displacement synthesis is performed by using a DNA polymerase having a strand displacement activity (such as Bst DNA polymerase (large fragment), Bst 2.0 DNA polymerase, phi29 DNA polymerase, DisplaceAce™ DNA Polymerase, etc.).

In the sequencing library provided in one of the embodiments of the present invention, the adaptor sequence contained in the insert fragment and the two copies of target sequence is arranged in an order of: 5' adaptor sequence (this adaptor sequence may not exist)-target sequence-linker-target sequence-3' adaptor sequence (the adaptor sequence may not exist), as shown in FIGS. 1, 2 and 3.

The sequencing library provided in the embodiments of the present invention is applicable to the sequencing platforms such as next generation and third-generation sequencing.

In the embodiments of the present invention, the adaptor sequence may contain a random base region of for example 2-30 bases, which is used as a tag to distinguish different target sequences.

In the present invention, a DNA amplification technology based on strand displacement reaction is used, and during the DNA amplification by strand displacement reaction, if certain DNA polymerases (e.g., Phi 29 DNA polymerase, or Bst DNA polymerase (large fragment)) meet a downstream DNA chain in the extension of a new strand, the extension reaction can be continued while the downstream double-stranded sequence is stripped to produce isothermal amplification of free single-stranded DNA. Normally, the DNA amplification based on strand displacement reaction requires no thermal denaturation. The DNA amplification based on strand displacement reaction includes strand displacement amplification, rolling circle amplification, multiple chain displacement amplification and loop-mediated amplification.

In the present invention, the next generation sequencing method refers to Sequencing by Synthesis, which is a method for determining the sequence of DNA by capturing a tag at a newly synthesized end, including, but not limited to, Roche/454 FLX, Illumina/Solexa Genome Analyzer and Applied Biosystems SOLID system.

In the present invention, the third-generation sequencing method refers to a single-molecule sequencing technology, that is, when the DNA sequencing is performed, sequencing of each DNA molecule can be achieved independently without PCR amplification. The third-generation sequencing method includes, but is not limited to, single molecule fluorescent sequencing, and the representative technology includes SMS from Helicos, SMART technology from Pacific Bioscience, and nanopore sequencing.

The sequencing library and use thereof provided in the present invention have at least the following beneficial effects:

1. At any depth of sequencing, errors in DNA amplification and sequencing can be effectively removed, so mutations in DNA molecules are accurately detected.

The adaptor sequence is ligated to the end of a small DNA fragment which is to be sequenced, then the chimera is denatured to obtain a DNA fragment having a single-stranded target sequence connected with the adaptor sequence, next single-stranded circularization is performed, a complementary strand of the single-stranded DNA is synthesized after the circularization, then nicking sites are nicked, and strand displacement is performed with a strand replacement enzyme. The two repeat units resulting from strand displacement replication are independent of each other during the amplification process, and therefore the errors generated during the replication of respective units are also independent. A sequencing library is constructed for the products and the library is sequenced; one or two repeat units are detected during each sequencing, the detected sequences of the two repeat units are mutually confirmed, the inconsistent bases of the two repeat units are the PCR error or sequencing error generated during the preparation of the library or the sequencing, and the consensus sequence is the primitive sequence.

The principle of the present invention is elucidated as follows, If sequencing machines have a sequencing error rate of 1/100 (the error rate of the next generation sequencing is from 1/100 to 1/1000), the probability of one type of error occurring simultaneously at the same sites on two repeat units in a consensus sequence is: $1/3*(1/100)^2$, that is, an error rate of $3*10^{-5}$ (the error rate of the consensus base on more repeat units is much lower). The probability of the same error occurring in two different consensus sequences is: $(1/3*(1/100)^2)^2$, that is., $9*10^{-10}$. Therefore, by using this method, the errors occurring during the library construction and sequencing are effectively removed, thereby achieving the purpose of accurate sequencing.

2. Uniform genome sequencing is achieved with the uniform amplification of DNA sequences to be tested.

In the double-nicking strand displacement amplification employed in the present method, one original DNA is only allowed to amplify four times, by which the rapid amplification of certain easy-to-be-amplified sequences and the slow or even failed amplification of certain difficult-to-beamplified regions in a certain time during rolling circle amplification are effectively avoided. The present invention effectively eliminates the extreme bias of the rolling circle amplification and achieves an effective and uniform coverage of the genome.

3. The present invention is compatible with the target region capture sequencing (e.g., exon capture sequencing, target gene capture sequencing, target gene screening) and other methods.

Figure 4:
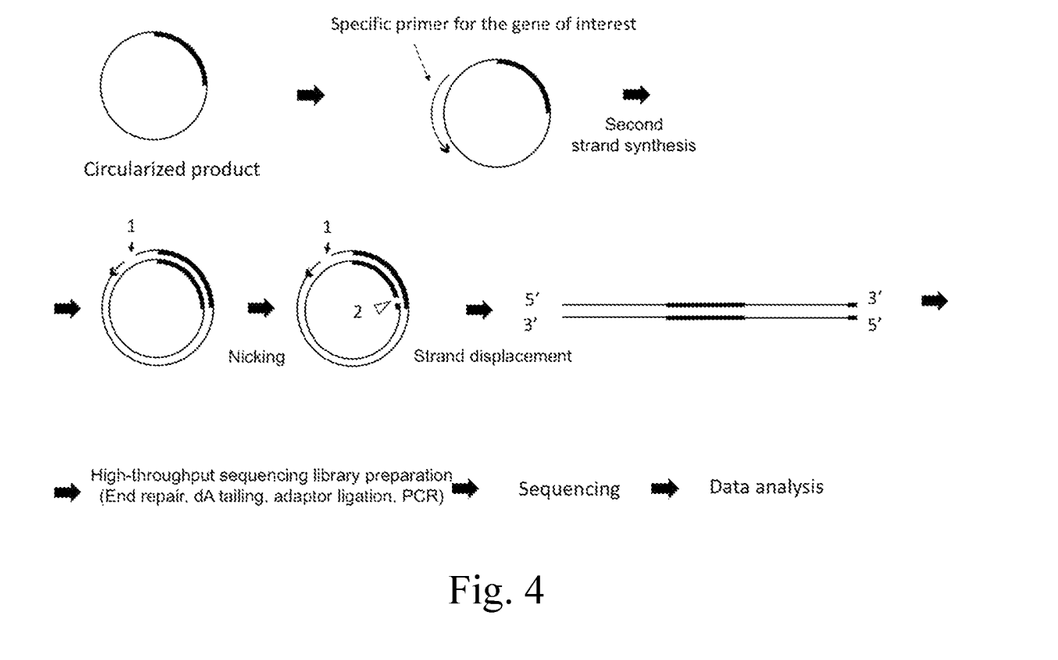
FIG. 4 shows use of the method in screening the genes of interest, where a complementary strand of a circularized DNA molecule is synthesized by using a primer matching with the gene of interest (one or more), then nicking is performed, and a sequencing library is constructed after strand displacement synthesis, thereby effectively enriching the genes of interest and realizing the sequencing of the genes of interest.

In the sequence consisting of an adaptor sequence and two copies of target sequence provided in the present invention, the two copies copied from the original DNA are linked in tandem and are mutually independent sequences. During the target region capture, the molecule captured by the probe contains at least the nucleic acid sequences of two direct repeat units, and when the captured sequence is sequenced, the DNA sequence can be precisely detected. When target gene screening is used, if the circularization is single-strand circularization, a complementary strand of the circularized DNA molecule is directly synthesized by using a primer matching with the target gene (one or more); if the circularization is double-stranded circularization, the double-stranded sequence is denatured, and then a complementary strand of the circularized DNA molecule is synthesized by using a primer matching with the target gene (one or more), thereby enriching the genes of interest only, as shown in FIG. 4.

4. The present invention is suitable for the construction of a sequencing library for a small amount of short DNA fragments or even a single-stranded DNA sequencing library.

The fragments are short (30-200 base pairs). The present invention is suitable for the construction of a sequencing library for severely degraded DNA such as free DNA in peripheral blood, ancient fossils and so on, due to the small starting amount of DNA (nanogram level or lower) and short fragments required for single-stranded circularization.

5. The sequence consisting of a linker sequence and two copies of target sequence constructed by the present method is useful in the construction of a variety of next generation sequencing libraries of short segments, thus being applicable to various sequencing platforms.

BRIEF DESCRIPTION OF THE DRAWINGS

FIG. 1 is a flow chart of a process for constructing a sequencing library according to the present invention (by using a primer without a nicking base). A DNA macromolecule is fragmented and ligated to an adaptor with a nicking base (such as dUTP, 8-oxo-dGTP, nicking endonuclease recognition site, etc.) followed by single-stranded circularization. A complementary strand of the circularized DNA molecule is synthesized by using an ordinary primer without a nicking base, a gap is generated by nicking (where according to the nicking base in the adaptor, an appropriate nicking mode is selected), and the sequence consisting of the linker and two copies of the target sequence is subjected to strand displacement. A standard high-throughput sequencing library is constructed by using the double-stranded DNA after the strand displacement, and sequenced, and the data is analyzed.

FIG. 2 is a flow chart of a process for constructing a sequencing library according to the present invention (by using a primer with a nicking base). A DNA macromolecule is fragmented and ligated to an adaptor with a nicking base (such as dUTP, 8-oxo-dGTP, and nicking endonuclease recognition site, etc.), followed by single-stranded circularization. A complementary strand of the circularized DNA molecule is synthesized by using a primer with a nicking base, a nick or a gap is generated by nicking (where according to the nicking base in the adaptor, an appropriate nicking mode is selected), and the sequence consisting of the linker and two copies of the target sequence is subjected to strand displacement. A standard high-throughput sequencing library is constructed by using the double-stranded DNA after the strand displacement, and sequenced, and the data is analyzed.

DETAILED DESCRIPTION

The implementations of the present invention are described in detail below with reference to the embodiments. However, those skilled in the art will understand that the following embodiments are provided solely for illustrating the present invention and are not intended to limit the scope of the present invention. In the embodiments, where no specific conditions are given, normal conditions or the conditions suggested by the manufacturer are followed. Reagents or instruments without specified manufacturers are all commercially available conventional products.

One of the innovative points of the present invention is that a double-stranded circular DNA molecule with double nicks/gaps, triple nicks/gaps or multiple nicks/gaps is obtained by ligating a short DNA molecule with an adaptor sequence and nicking after single-stranded or double-stranded circularization, and then amplified by using a strand displacement enzyme to obtain a sequence consisting of two target sequences which have at least partially the same region connected by one linker, and a sequencing library is constructed and then sequenced. Specifically, the present invention can be implemented through at least the following solutions.

Scheme 1 (Double-Gap Scheme by Single-Stranded Circularization):

The DNA is first randomly fragmented into a fragment having a length that is less than half the sequencing read length of a next generation sequencing machine (where the sum of the length after the fragmentation and the length of the 5' adaptor sequence is preferably less than half the read length), and then the adaptor sequence is ligated, where the adaptor sequence contains a nicking base (e.g., dUTP, 8-oxo-dGTP, and a nicking endonuclease recognition site, etc.). The DNA is denatured at a high temperature and then cooled immediately to form a single-stranded sequence. The single-stranded DNA containing the adaptor sequence is circularized by using a single-stranded ligase. A complementary strand of the circularized DNA molecule is synthesized by using an ordinary primer without a nicking base, a nick/gap is generated by nicking (where according to the nicking base in the adaptor, an appropriate nicking mode is selected), and the sequence is subjected to strand displacement synthesis. A standard high-throughput sequencing library is constructed by using the double-stranded DNA after the strand displacement, and sequenced, and the data is analyzed.

Scheme 2 (Triple-Gap and Multi-Gap Scheme by Single-Stranded Circularization):

The DNA is first randomly fragmented into a fragment having a length that is less than half the sequencing read length of a next generation sequencing machine (where the sum of the length after the fragmentation and the length of the 5' adaptor sequence is preferably less than half the read length), and then the adaptor sequence is ligated, where the adaptor sequence contains a nicking base (e.g., dUTP, 8-oxo-dGTP, and a nicking endonuclease recognition sites, etc., and the number of the nicking base is not limited). The DNA is denatured at a high temperature and then cooled immediately to form a single-stranded sequence. The single-stranded DNA containing the adaptor sequence is circularized by using a single-stranded ligase. A complementary strand of the circularized DNA molecule is synthesized by using a primer with a nicking base (e.g., dUTP, 8-oxo-dGTP, and a nicking endonuclease recognition sites, etc., and the number of the nicking base is not limited), a nick/gap is generated by nicking (where according to the nicking base in the adaptor, an appropriate nicking mode is selected), and the sequence is subjected to strand displacement synthesis. A standard high-throughput sequencing library is constructed by using the double-stranded DNA after the strand displacement and sequenced, and the data is analyzed.

Scheme 3 (Double-Stranded Circularization)

The DNA is first randomly fragmented into a fragments having a length that is less than half the sequencing read length of a next generation sequencing machine (where the sum of the length after the fragmentation and the length of the 5' adaptor sequence is preferably less than half the read length), and then the adaptor sequence is ligated, where the adaptor sequence contains a nicking base (e.g., dUTP, 8-oxo-dGTP, and a nicking endonuclease recognition site, etc.), or the DNA molecule or the adaptor sequence is dephosphorylated during the circularization. A DNA ligase is used for double-stranded circularization. For the circularized DNA molecule, a gap is generated by nicking (where according to the nicking base in the adaptor, an appropriate nicking mode is selected, and if there is a gap in the adaptor, or the adaptor is dephosphorylated, the nicking is omitted), and the sequence is subjected to strand displacement synthesis. A standard high-throughput sequencing library is constructed by using the double-stranded DNA after the strand displacement, and sequenced, and the data is analyzed.

EXAMPLE 1

Construction of a Whole Genomic DNA Library According to Scheme 1 (Double-Gap Scheme) (Illumina Platform)

1) DNA Fragmentation
Instruments and reagents:
Ultrasonic breaking device: Covaris: S2 Focused-ultrasonicator
Breaking tube: Covaris Microtube 6*16 mm, catalog #: 520045
QIAGEN MinElute Gel Extraction Kit (250), Catalog #: 28606
Takara 20 bp DNA Ladder (Dye Plus), Takara Code, 3420A
5 μg of the purified PhiX 174 genomic DNA was broken into a fragment of 150-200 bp by using an ultrasonic breaking device (Covaris S2 Focused-ultrasonicator) (Intensity: 5, Duty Cycle: 10%, Cycles per Burst: 200, Temperature: 4° C., time: 60s, number of cycles: 5) in 50 μl of a breaking system.

After 4% agarose gel electrophoresis (80V, 70 min; 1× TAE), and gel extraction (QIAGEN MinElute Gel Extraction Kit), the fragment of 60-90 bp was recovered (Takara 20 bp DNA Ladder), as detailed in the instruction of QIAGEN MinElute Gel Extraction Kit.

2) End Repair A-Tailing
Reagents: New England Biolabs: NEBNextx® Ultra™ DNA Library Prep Kit for Illumina®, Catalog #: E7370S
DNA fragment: 55.5 μl
End Prep Enzyme Mix: 3 μl
End Repair Reaction Buffer (10×): 6.5 μl
In total: 65 μl
30 min at 20° C., and 30 min at 65° C.

3) Ligation of the Adaptor Sequence
Reagents: New England Biolabs: NEBNext® Ultra™ DNA Library Prep Kit for Illumina®, Catalog #: E7370S
Blunted DNA: 65 μl
Blunt/TA Ligase Master Mix: 15 μl
Ligation Enhancer: 1 μl
Adaptor sequence: UO-A (50 pmol): 2 μl
In total: 83 μl
30 min at 20° C., 5 min at 65° C., followed by immediately standing on the ice for 3 min.

The product was purified with Agencourt AMPure XP magnetic beads (Beckman Coulter, Inc).

Adaptor sequences: UO-A was formed by mixing 100 pmol of UO-adaptor1 (dissolved in an annealing buffer: 10 mM Tris-HCl (pH 7.5), 1 mM EDTA, 0.1 mM NaCl) and 100 pmol of UO-adapter2 (dissolved in an annealing buffer: 10 mM Tris-HCl (pH 7.5), 1 mM EDTA, 0.1 mM NaCl) in equal volumes and annealing (5 min at 94° C., and then gradually cooling to 25° C. at 0.1° C. per second).

```
UO-adaptor1:
                                        (SEQ ID NO: 1)
5'-pGATCAGTCGTACGTGCTTACTCTCAATAGCAGCTT-3'

UO-adaptor2:
                                        (SEQ ID NO: 2)
5'-pGTGGGCAGTCGGTGAACGACTGAUCT-3'
```

Note: Adaptor sequences include, but are not limited to, the sequences of UO-adapter1 and UO-adapter2 in the example. The same below.

4) Single-Stranded Circularization

New England Biolabs: Exonuclease I (E. coli), Catalog #: M0293

New England Biolabs: Exonuclease III (E. coli), Catalog #: M0206

Epicentre: CircLigase II ssDNA Ligase, Catalog #: CL9025K

DNA: 24 μl 3 min at 95° C., followed by immediately standing on the ice for 3 min    10× circligase buffer: 6 μl
   10 mmol $MnCl_2$: 1.5 μl
   Circligase (100 Oil): 1.5 μl
   2 h at 60° C., and 10 min at 80° C.
   Digestion of linear and dimeric DNA:
   Exonuclease I (E. coli): 1 μl
   Exonuclease III (E. coli): 1 μl
   1 h at 37° C.

The product was purified with MinElute Reaction Cleanup Kit.

5) Complementary Strand Synthesis

New England Biolabs: Klenow Fragment (3'→5' exo-), Catalog #: M0212S

New England Biolabs: USER™ Enzyme, Catalog #: M5505S

NEB buffer 4: 2 μl
   primer (UO-p1, 10 uM): 1 μl
   DNA: 15.8 μl 3 min at 95° C., followed by immediately standing on the ice for 3 min.

After that, the following was added:
   2.5 mM dNTP: 0.5 μl
   100× BSA: 0.2 μl
   Klenow Fragment (3'→5' exo-): 1 μl
   In total: 20 μl
   30 min at 20° C. and 20 min at 75° C.
   USER™ Enzyme: 1 μl
   30 min at 37° C.

The product was purified with Agencourt AMPure XP magnetic beads (Beckman Coulter, Inc).

```
UO-p1:
                                    (SEQ ID NO: 3)
5'-AGCACGTACGACTGATCT-3'
```

6) Strand Displacement Synthesis

New England Biolabs: Bst 2.0 WarmStart® DNA Polymerase, Catalog #: M0538S

DNA: 16.5 μl
   Isothermal Amplification Buffer: 2 μl
   2.5 mM dNTP: 0.5 μl
   Bst 2.0 WarmStart® DNA Polymerase: 0.5 μl
   30 min at 60° C.

The product was purified with Agencourt AMPure XP magnetic beads (Beckman Coulter, Inc).

7) Construction of the Illumina Library by Using the Sequence

Commercial kits for constructing standard Illumina libraries such as TruSeq DNA Sample Preparation Kits and so on were used. The construction included the following steps specifically:

(1) End repair A-tailing (the same as the "end repair A-tailing" section above)

(2) Ligation of adaptor sequence for sequencing

Blunted DNA: 65 μl
   Blunt/TA Ligase Master Mix: 15 μl
   Ligation Enhancer: 1 μl NEXTflex™ DNA Barcodes (Bioo Scientific Corporation, Catalog #:514101): 0.5 μl, in total: 83 μl 30 min at 20° C.

The product was purified with Agencourt AMPure XP magnetic beads (Beckman Coulter, Inc).

(3) PCR amplification

DNA: 24 μl
   NEXTflex™ Primer Mix (Bioo Scientific Corporation, Catalog #: 514101): 1 μl
   KAPA HiFi HotStart ReadyMix (Kapa Biosystems, Catalog #: KK2601): 25 μl
   In total: 50 μl Cycling conditions for PCR amplification:

pre-denaturation for 45 s at 98° C., amplification by 13 cycles of (15 s at 98° C., 30 s at 65° C., and 60 s at 72° C.), 4 min at 72° C., cooling at 4° C.

The product was purified with Agencourt AMPure XP magnetic beads (Beckman Coulter, Inc).

After 2% agarose gel electrophoresis and gel extraction (QIAGEN MinElute Gel Extraction Kit), the fragment of 300-500 bp was recovered.

The eluted DNA was the constructed library which can be sequenced on a next generation sequencing platform.

EXAMPLE 2

Construction of a Whole Genomic DNA Library According to Scheme 2 (with the Triple-Gap Scheme as an Example)

(1) The DNA fragmentation, end repair A-tailing, adaptor ligation and single-stranded circularization steps were the same as those in Example 1.

(2) Complementary strand synthesis

New England Biolabs: Klenow Fragment (3'→5' exo-), Catalog #: M0212S

New England Biolabs: USER™ Enzyme, Catalog #: M5505S

NEB buffer 4: 2 μl
   primer (UO-p1-2, 10 uM): 1 μl
   DNA: 15.8 μl 3 min at 95° C., followed by immediately standing on the ice for 3 min.

After that, the following was added:
   2.5 mM dNTP: 0.5 μl
   100× BSA: 0.2 μl
   Klenow Fragment (3'→5' exo-): 1 μl
   In total: 20 μl
   30 min at 20° C., 20 min at 75° C.
   USER™ Enzyme: 1 μl
   30 min at 37° C., 5 min at 50° C., followed by immediately placing on ice.

The product was purified with Agencourt AMPure XP magnetic beads (Beckman Coulter, Inc).

```
UO-p1-2:
                                    (SEQ ID NO: 4)
5'-AGCACGTACGACTGAUCT-3'
```

The product can then be used for constructing next generation and third-generation sequencing libraries.

EXAMPLE 3

Construction of a Whole Genomic DNA library according to Scheme 3 (Double-Stranded Circularization, where the Adaptor Containing a Nicking Site)

(1) DNA fragmentation (about 700 bp, fragmentation conditions: duty cycle: 5%, intensity: 3, cycles per burst: 200, time: 75 s), the end repair A-tailing and adaptor ligation were the same as those in Example 1, the adaptor sequence was UO-A2 annealed by the following two sequences:

```
                                              (SEQ ID NO: 5)
     5'-AGCACGTACGACTGAUCT-3'

(SEQ ID NO: 6)
     5'-pGATCAGTCGTACGTGCT-3'
```

(2) End phosphorylation
44 µl DNA, 10U T4 PNK (T4 Polynucleotide Kinase, NEB, M0201S), 50 mM Tris-HCl pH 7.5, 10 mM MgCl2, 1 mM ATP, 10 mM DTT, 30 min at 37° C., and the product was purified by 1× Ampure XP magnetic beads.

(3) Double-stranded circularization
NEBNext® Quick Ligation Module (NEB, E6056S)
DNA: 35 µl
T4 quick ligase: 5 µl
5× ligase buffer: 10 µl
30 min at 20° C.
The product was purified with 1× Ampure XP magnetic beads.

(4) Enzymatic digestion
Exonuclease I (E. coli): 1 µl
Exonuclease III (E. coli): 1 µl
USER™ Enzyme: 1 µl
DNA: 42 µl
NEB buffer 4: 5 µl
1 h at 37° C.
The product was purified with MinElute Reaction Cleanup Kit.

(5) Strand displacement synthesis
New England Biolabs: Bst 2.0 WarmStart® DNA Polymerase, Catalog #: M0538S
DNA: 16.5 µl
Isothermal Amplification Buffer: 2 µl
2.5 mM dNTP: 0.5 µl
Bst 2.0 WarmStart DNA Polymerase: 0.5 µl
60 min at 60° C.
The product was purified with Agencourt AMPure XP magnetic beads (Beckman Coulter, Inc).
The product can be used for constructing the first-, second- and third-generation sequencing libraries.

EXAMPLE 4

Construction of a Whole Genomic DNA Library According to Scheme 3 (Double-Stranded Circularization)

(1) DNA fragmentation (about 700 bp, fragmentation conditions: duty cycle: 5%, intensity: 3, cycles per burst: 200, time: 75 s), end-repair A-tailing (2) 5' dephosphorylation (NEB: M0289)
DNA: 44 µl
Antarctic Phosphatase: 1 µl
Antarctic Phosphatase Reaction Buffer: 5 µl
60 min at 37° C., the product was purified with 1× Ampure XP magnetic beads.

(3) Double-stranded circularization
NEBNext® Quick Ligation Module (NEB, E6056S)
DNA: 34 µl
UO-A3: 1 µl
T4 quick ligase: 5 µl
5× ligase buffer: 10 µl
30 min at 20° C.
The product was purified with 1× Ampure XP magnetic beads.

Adaptor sequence was UO-A3 annealed by the following two sequences:

```
                                              (SEQ ID NO: 7)
     5'-pGATCAGTCGTACGTGCTTACTCTCAATAGCAGCTT-3'

(SEQ ID NO: 8)
     5'-pAGCTGCTATTGAGAGTAAGCACGTACGACTGATCT-3'
```

(4) Enzymatic digestion
Exonuclease I (E. coli): 1 µl
Exonuclease III (E. coli): 1 µl
DNA: 43 µl
NEB buffer 4: 5 µl
1 h at 37° C.
The product was purified with MinElute Reaction Cleanup Kit.

(5) Strand displacement synthesis
New England Biolabs: Bst 2.0 WarmStart® DNA Polymerase, Catalog #: M0538S
DNA: 16.5 µl
Isothermal Amplification Buffer: 2 µl
2.5 mM dNTP: 0.5 µl
Bst 2.0 WarmStart® DNA Polymerase: 0.5 µl
60 min at 60° C.,
The product was purified with Agencourt AMPure XP magnetic beads (Beckman Coulter, Inc).
The product can be used for constructing the first-, second- and third-generation sequencing libraries.

EXAMPLE 5

Construction of a Target Region Capture Library

A library of human genomic DNA was constructed according to the method of Example 1, and the target regions of the PCR product were captured.

Exon Probe Hybridization
Exon probe hybridization was performed on the PCR product by using SureSelect Human All Exon Kits from Agilent in this experiment. Formulation of hybridization buffer:
SureSelect Hyb #1 (orange cap, or bottle): 25 µl
SureSelect Hyb #2 (red cap): 1 µl
SureSelect Hyb #3 (yellow cap): 10 µl
SureSelect Hyb #4 (black cap, or bottle): 13 µl
In total: 49 µl, 5 min at 65° C.
Formulation of capture library mixture:
SureSelect Library: 5 µl
SureSelect RNase Block (purple cap): 0.5 µl
ddH2O: 1.5 µl
In total: 7 µl, 2 min at 65° C.

Formulation of sample mixture:
Purified DNA (about 700 ng): 3.4 µl
SureSelect Indexing Block #1 (green cap): 2.5 µl
SureSelect Block #2 (blue cap): 2.5 µl
SureSelect Indexing Block #3 (brown cap): 0.6 µl
In total: 9 µl, 5 min at 95° C., held at 65° C.

13 µl of hybridization buffer prepared was added to the capture library mixture (7 µl), then the sample mixture (9 µl) was added to give a total volume of 29 µl, and hybridization was performed at 65° C. for 24 h.

Hybridized fragments were captured by the magnetic beads (Invitrogen™: Dynabeads® M-280 Streptavidin, Catalog #: 11205D) (50 µl magnetic beads were washed three times with 200 µl SureSelect Binding Buffer, and then resuspended in 200 µl SureSelect Binding Buffer; the hybridized product was added, stood at room temperature for 30 min, and adsorbed onto the magnetic beads; the magnetic beads were washed once with SureSelect Wash 1, three times with SureSelect Wash 2, and then resuspended in 36.5 µl ddH$^2$O), as detailed in the instruction manual of SureSelect Human All Exon Kits from Agilent.

(7) PCR after probe hybridization
Instruments and reagents:
PCR machine: Eppendorf: Mastecycler pro s
Agilent: Herculase II Fusion DNA Polymerases, Catalog #: 600677
Beckman Coulter, Inc: Agencourt AMPure XP, Item No. A63880
The reaction formula was as follows:
Resuspended magnetic beads in exon probe hybridization: 36.5 µl
MP PCR primer 1.0 (10 pmol): 1 µl
MP PCR primer 2.0 (10 pmol): 1 µl
5× Herculase II Reaction Buffer: 10 µl
dNTPs (100 mM; 25 mM each dNTP): 0.5 µl
Herculase II Fusion DNA Polymerase: 1 µl
In total: 50 µl.
Cycling conditions for PCR amplification:
pre-denaturation for 2 min at 98° C., amplification by 12 cycles of (30 s at 98° C., 30 s at 65° C., 30 s at 72° C.), 10 min at 72° C., cooling at 4° C.
Primer sequences:

```
MP PCR primer 1.0:
                                        (SEQ ID NO: 9)
5'-AATGATACGGCGACCACCGAGATCTACACTCTTTCCCTACACGACGC
TCTTCCGATCT-3'

MP PCR primer 2.0:
                                       (SEQ ID NO: 10)
5'-CAAGCAGAAGACGGCATACGAGAT-3'
```

After PCR, the product was purified with Agencourt AMPure XP magnetic beads and the steps were summarized as follows. 1.8 times the volume of beads were added to the amplified product, the product was stood and adsorbed onto the magnetic beads for 5 minutes at room temperature. The supernatant was removed, the magnetic beads were washed twice with 70% alcohol, air dried and eluted with 16 µl ddH$_2$O, as detailed in the instruction for the kit.

The eluted DNA was the constructed human exon library which can be used for the sequencing by the next generation sequencing platform.

EXAMPLE 6

DNA Library Construction of free DNA in Peripheral Blood (1) Extraction of free DNA in peripheral blood and determination of fragment size Instruments and reagents:
QIAGEN: QIAamp Circulating Nucleic Acid Kit, catalog #: 55114
Agilent: 2100 bioanalyzer 2 ml of plasma was taken, plasma DNA (cell-free circulating DNA) was extracted with QIAamp Circulating Nucleic Acid Kit from QIAGEN, and eluted with 20 µl of ddH$_2$O (as detailed in the instruction for the kit). The size distribution of the extracted fragments was tested with Agilent 2100 bioanalyzer. The results show that the sizes of the free DNA fragments in patients with liver cancer concentrate around 164 bp, the distribution range is about 110 bp-210 bp, the concentration is 4.78 ng/µl, and the total amount of DNA is about 100 ng.

(2) End repair A-tailing was performed on peripheral blood DNA, the adaptor ligation, single-stranded circularization, complementary strand synthesis, strand displacement, and subsequent Illumina library construction were the same as those in Example 1.

EXAMPLE 7

Analysis of Sequencing Data of Phage Phix174 Library in Example 1

Paired-end sequencing data of about 1 G (where read length is 2×125=250 bp) was obtained with hiseq 2500. The data analysis is as follows:

1. There are 1,410,463 reads in total, where the number of reads of correct structure is 631,353.

2. The size range of the target sequence is 30-107 bp with an average size of 91.87 bp, a standard deviation of 14.42 and a median of 94 bp.

3. Paired-End high-throughput sequencing is performed on the constructed library. The two target sequences from one paired sequencing read are compared with each other and inconsistent sequences are removed. Sequencing error rate refers to, in the consensus sequence, the proportion of the sites which are not the same as the reference sequence. The error rate of DNA in the tested data is calculated based on this principle. Assuming that there is no low-frequency mutation in the sample, the sequencing error rate of this method is $10^{-5}$. The distribution of sequencing errors on different bases (based on reference genome) is different. See Table 1.

TABLE 1

Sequencing error rate of different bases measured by the method described.

| Sequencing error type | Error rate |
|---|---|
| A => C | 1.85E−06 |
| T => G | 1.25E−06 |
| A => G | 6.56E−06 |
| T => C | 7.55E−06 |
| A => T | 3.59E−06 |
| T => A | 2.80E−06 |
| C => A | 3.11E−05 |
| G => T | 3.22E−05 |
| C => G | 9.94E−06 |
| G => C | 7.42E−06 |
| C => T | 1.67E−05 |
| G => A | 1.34E−05 |

The calculation results show that the single base error rate ($10^{-5}$) of this method is much lower than the error rate (1%) of the next generation sequencing, and is far lower than the error rate of some existing improved methods. Therefore, the method almost completely eliminates the problem of high error rate of the next generation sequencing and realizes the precise sequencing of DNA molecules by means of the next generation sequencing platform.

4. Distribution of sequencing coverage

Based on the sequencing results, the coverage of the detected sequence on the whole phix174 genome is analyzed. The result shows that the bias of amplification is effectively reduced by adopting the method provided in the present invention and the sequencing data achieves the effective and uniform coverage on the whole genome.

If the starting template is fully evenly amplified, then the sequencing depth at any site in the genome should be equal to the average genome-wide sequencing depth, i.e., the ratio should be 1, and after taking the denary logarithm of the ratio, the result should be 0. If the starting template cannot be amplified uniformly, the sequencing depth at certain sites in the genome is evidently not equal to the average genome-wide sequencing depth, i.e., the ratio is greater than 1 or less than 1, and the logarithm of the ratio should be greater than or less than 0.

With the libraries constructed in Chinese Patent Nos. 201310651462.5 and 201410448968.0, the logarithms of the ratios of the depth of sequencing at almost all sites to the average depth of genome-wide sequencing are seriously deviated from 0, in which the logarithms of the ratios concentrate below−1 for a majority of sites, and are greater than 0, or even up to 4 for a small portion of sites, which means that the replication multiple at some sites is tens to hundreds times the average genome-wide replication multiple. This is because the great bias of rolling circle replication during circular DNA amplification leads to high amplification at certain sites, and the presence of the sites of high amplification increases the average depth of the genome-wide sequencing, resulting in reduced ratio of the sequencing depth at the majority of sites to the average depth of the genome-wide sequencing. In the present invention, the logarithms of the ratios of the depth of sequencing at almost all sites to the average depth of genome-wide sequencing are uniformly distributed around 0. Even at the site of biggest bias, the ratio of the sequencing depth to the genome-wide sequencing depth is also less than 1. Uniform replication of the whole genome is achieved and the amplification product covers the whole genome better and more uniformly. In summary, by the technology provided in the present invention, the circular DNA molecules are effectively and uniformly amplified.

Another advantage of this technology is that the accuracy of sequencing is independent of the depth of sequencing, unlike tagging methods can only determine the DNA sequence accurately at a very high depth of sequencing, this approach can achieve the accurate sequencing of large genomes (such as human genome, etc.).

By using the method of the present invention, the molecular composition of DNA in cells can be accurately determined and the DNA composition in a normal or diseased (such as cancer tissue) cell population can be presented more realistically. In the detection of cancers, whether potential carcinogenic mutation has occurred to a tissue or organ of a normal individual can be detected to achieve the purpose of early diagnosis and prevention of cancers. In the field of cancer research, the method can be used for detecting the distribution of DNA mutations in populations with cancers; for finding potential small clonal populations in cancer tissues to truly understand the heterogeneous structure of tumors; for elucidating the role of mutations in the development of cancers; and for finding cancer stem cells and so on. In the treatment of cancers, the method can be used for finding cancer stem cell populations, and then specific drug targets for cancer stem cells are designed to achieve the effective treatment for cancers. For normal individuals, the method can be used for detecting DNA mutations in normal cells of the individuals to trace the phylogenetic linage of normal tissues; the method can also be used for calculating the number of DNA mutations in a tissue of individuals of different ages to estimate the rate of DNA mutation; and the method can be used for detecting whether there are mutations associated with various diseases in a normal individual, so as to prevent the occurrence of diseases.

Also, the method is effective in the construction of libraries of free DNA in peripheral blood and in detection of low-frequency mutation sites in peripheral blood, such that the effective detection and evaluation of occurrence and development of cancers and harmful mutations to fetus in prenatal diagnosis can be achieved in a non-invasive detection way.

Ancient human DNA sequencing is the main means to study human evolution, but there are many problems in ancient human DNA sequencing. Among them, the most serious problems are low amount of extracted ancient human DNA, severe degradation and severe microbial contamination. The method can be used for constructing libraries with a very small amount of DNA (single or double-stranded); and the constructed library can be used for capturing exon (after removing microbial contamination on the genome), thereby effectively solving the problems in the construction of ancient DNA library.

Based on the present invention, a sequencing library construction kit is provided, which comprises an end repair A-tailing reagent, a DNA ligase, an adaptor sequence, a single-stranded circularization reagent, a second-strand synthesis reagent, a nicking enzyme, a strand replacement reagent, dNTPs (2.5 mM) and BSA (100×). The kit can specifically comprise the followings:

End repair A-tailing agent: comprising 10× end repair A-tailing buffer (500 mM Tris-HCl, 100 mM $MgCl_2$, 100 mM DTT, 10 mM ATP, 4 mM dATP, 4 mM dCTP, 4 mM dGTP, 4 mM dTTP, pH 7.5, 25° C.), T4 DNA Polymerase (3 U/μl), Klenow DNA Polymerase (0.5 U/μl), T4 Polynucleotide Kinase (10 U/μl, Thermophilic modified DNA polymerase (5 U/μl).

DNA ligase: T4 DNA ligase (20 U/μl), 5×T4 DNA ligase buffer (250 mM Tris-HCl, 50 mM $MgCl_2$, 5 mM ATP, 50 mM DTT, pH 7.5, 25° C.)

Adaptor sequence:

Y-shaped structure formed by annealing 5'-pGATCAGTCGTACGTGCTTACTCT-CAATAGCAGCTT-3' (SEQ ID NO: 1) and 5'-pGTGGGCAGTCGGTGAACGACTGAUCT-3'(SEQ ID NO: 2)

Single-stranded circularization reagent: a single-stranded cyclase (100 U/μl), 50 mM $MnCl_2$, 10× single-stranded cyclase buffer (0.33 M Tris-Acetate (pH 7.5), 0.66 M potassium acetate and 5 mm DTT Second-strand synthesis reagent: DNA Polymerase I (E. coli) (10 U/μl) 10× Buffer: (500 mM NaCl, 100 mM, Tris-HCl, 100 mM $MgCl_2$, 10 mM DTT, pH 7.9, @25° C.

Nicking enzyme: Uracil DNA glycosylase (UDG) (1 U/μl), DNA glycosylase-lyase Endonuclease VIII (1 U/μl)

Strand displacement reagent: Bst DNA polymerase large fragment (8 U/μl), 10× Bst DNA polymerase buffer (200 mM Tris-HCl, 100 mM $(NH_4)_2SO_4$, 100 mM KCl, 20 mM $MgSO_4$, 1% Triton® X-100, pH 8.8, @25° C.)

Although specific embodiments of the present invention have been described in detail, those skilled in the art will understand that various modifications and replacements can be made to those details based on all the teachings disclosed, which are all contemplated in the scope of the present invention as defined the appended claims and any equivalents thereof.

What is claimed is:

1. A method for preparing a polynucleotide for sequencing, the polynucleotide comprising a linker and exactly two target sequences, wherein the two target sequences are respectively linked to two ends of the linker, the nucleotide sequence of each of the target sequences is different from the nucleotide sequence of the linker, and the two target sequences are direct repeat sequences, the method comprising:
   obtaining a double-stranded circular polynucleotide having nicks or gaps in both strands; and
   subjecting the double-strands circular polynucleotide with nicks or gaps in both strands to strand displacement amplification, forming the polynucleotide for sequencing.

2. The method of claim 1, wherein a reverse complementary region exists in the linker.

3. The method of claim 1, wherein one end of at least one of the target sequences opposing the end linked with the linker is further linked with an additional sequence which is not a target sequence, and at least part of the region of the additional sequence is the same as part of a region of the linker.

4. The method of claim 1, wherein a length of the target sequence is less than a sequencing read length of a DNA sequencing machine.

5. The method of claim 3, wherein a sum of lengths of the additional sequence and the target sequences is less than a sequencing read length of a DNA sequencing machine.

6. The method of claim 1, wherein a length of the target sequence is less than a sequencing read length of a DNA sequencing machine.

7. A method for preparing a polynucleotide for sequencing, the polynucleotide consisting of a linker and exactly two target sequences, wherein the two target sequences are respectively linked to the two ends of the linker, the nucleotide sequence of each of the target sequence is different from the nucleotide sequence of the linker, and the two sequences are direct repeat sequences, the method comprising:
   obtaining a double-stranded circular polynucleotide having nicks or gaps in both strands; and
   subjecting the double-strands circular polynucleotide with nicks or gaps in both strands to strand displacement amplification, forming the polynucleotide for sequencing.

8. A method for preparing a sequencing library, comprising the steps of:
   obtaining a double-stranded circular polynucleotide having nicks or gaps in both strands; and
   subjecting the double-strands circular polynucleotide with nicks or gaps in both strands to strand displacement amplification, forming polynucleotide, subjecting the polynucleotide to a standard high-throughput sequencing library preparation;
   wherein the polynucleotide comprises a linker and two target sequences, two ends of the linker are respectively linked to the target sequences, and the two target sequences are direct repeat sequences.

* * * * *

SEQUENCE LISTING

```
<160> NUMBER OF SEQ ID NOS: 10

<210> SEQ ID NO 1
<211> LENGTH: 35
<212> TYPE: DNA
<213> ORGANISM: Artificial
<220> FEATURE:
<223> OTHER INFORMATION: adaptor

<400> SEQUENCE: 1
gatcagtcgt acgtgcttac tctcaatagc agctt                                 35

<210> SEQ ID NO 2
<211> LENGTH: 26
<212> TYPE: DNA
<213> ORGANISM: Artificial
<220> FEATURE:
<223> OTHER INFORMATION: adaptor

<400> SEQUENCE: 2
gtgggcagtc ggtgaacgac tgauct                                           26

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
agcacgtacg actgatct                                                    18

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
agcacgtacg actgauct                                                    18

<210> SEQ ID NO 5
<211> LENGTH: 18
<212> TYPE: DNA
<213> ORGANISM: Artificial
<220> FEATURE:
<223> OTHER INFORMATION: adaptor

<400> SEQUENCE: 5
agcacgtacg actgauct                                                    18

<210> SEQ ID NO 6
<211> LENGTH: 17
<212> TYPE: DNA
<213> ORGANISM: Artificial
<220> FEATURE:
<223> OTHER INFORMATION: adaptor

<400> SEQUENCE: 6
gatcagtcgt acgtgct                                                     17

<210> SEQ ID NO 7
<211> LENGTH: 35
<212> TYPE: DNA
<213> ORGANISM: Artificial
```

```
<220> FEATURE:
<223> OTHER INFORMATION: adaptor

<400> SEQUENCE: 7
gatcagtcgt acgtgcttac tctcaatagc agctt                              35

<210> SEQ ID NO 8
<211> LENGTH: 35
<212> TYPE: DNA
<213> ORGANISM: Artificial
<220> FEATURE:
<223> OTHER INFORMATION: adaptor

<400> SEQUENCE: 8
agctgctatt gagagtaagc acgtacgact gatct                              35

<210> SEQ ID NO 9
<211> LENGTH: 54
<212> TYPE: DNA
<213> ORGANISM: Artificial
<220> FEATURE:
<223> OTHER INFORMATION: primer

<400> SEQUENCE: 9
aatgatacgg cgaccaccga gatctacact ctttccctac acgacgctct tccg         54

<210> SEQ ID NO 10
<211> LENGTH: 24
<212> TYPE: DNA
<213> ORGANISM: Artificial
<220> FEATURE:
<223> OTHER INFORMATION: primer

<400> SEQUENCE: 10
caagcagaag acggcatacg agat                                          24
```